(12) United States Patent
Marshall et al.

(10) Patent No.: US 7,384,414 B1
(45) Date of Patent: Jun. 10, 2008

(54) SAFETY PEN NEEDLE WITH NON-INJECTION END PASSIVE SAFETY FEATURES

(75) Inventors: William Marshall, Franklin Lakes, NJ (US); David R. Stonehouse, Cambridge (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/626,226

(22) Filed: Jan. 23, 2007

(51) Int. Cl.
*A61M 5/32* (2006.01)

(52) U.S. Cl. .................................. 604/198

(58) Field of Classification Search ............. 604/187, 604/198, 263, 110, 192, 195
See application file for complete search history.

(56) References Cited

U.S. PATENT DOCUMENTS

| | | | |
|---|---|---|---|
| 5,403,286 A | 4/1995 | Lockwood, Jr. et al. | 604/110 |
| 5,423,758 A | 6/1995 | Shaw | 604/110 |
| 5,545,145 A | 8/1996 | Clinton et al. | 604/192 |
| 5,725,508 A | 3/1998 | Chanoch et al. | 604/207 |
| 5,827,232 A | 10/1998 | Chanoch et al. | 604/208 |
| 5,928,205 A | 7/1999 | Marshall | 604/263 |
| 5,941,857 A * | 8/1999 | Nguyen et al. | 604/263 |
| 6,379,337 B1 | 4/2002 | Mohammad | 604/195 |
| 6,547,764 B2 | 4/2003 | Larsen et al. | 604/192 |
| 6,986,760 B2 | 1/2006 | Giambattista et al. | 604/198 |
| 7,104,969 B2 | 9/2006 | Du Plessis | 604/110 |
| 2005/0038392 A1* | 2/2005 | DeSalvo | 604/198 |
| 2005/0171485 A1* | 8/2005 | Larsen et al. | 604/198 |

* cited by examiner

*Primary Examiner*—Kevin C. Sirmons
*Assistant Examiner*—Deanna K. Hall
(74) *Attorney, Agent, or Firm*—Alan W. Fiedler; Fitzpatrick, Cella, Harper & Scinto

(57) ABSTRACT

A pen needle according to the invention comprises a needle hub having a recess for a pen injector and vial. When the pen injector is loaded into the hub, the needle cannula mounted in the hub pierces the septum of the vial. A non-patient end (non-injection end) shield positioned in the hub member engages the pen injector and travels with the pen injector when the pen injector is removed, to shield the non-patient of the needle. The shield is locked into place securing the person administering the injection from accidental injury from the non-patient end of the needle.

13 Claims, 3 Drawing Sheets

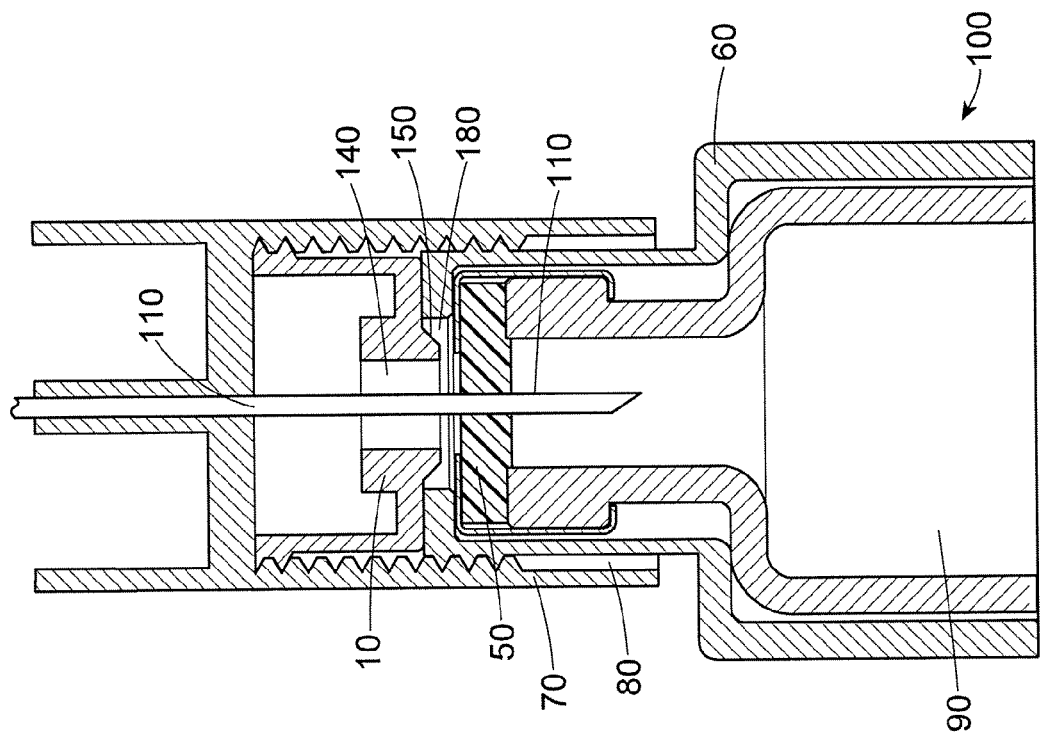
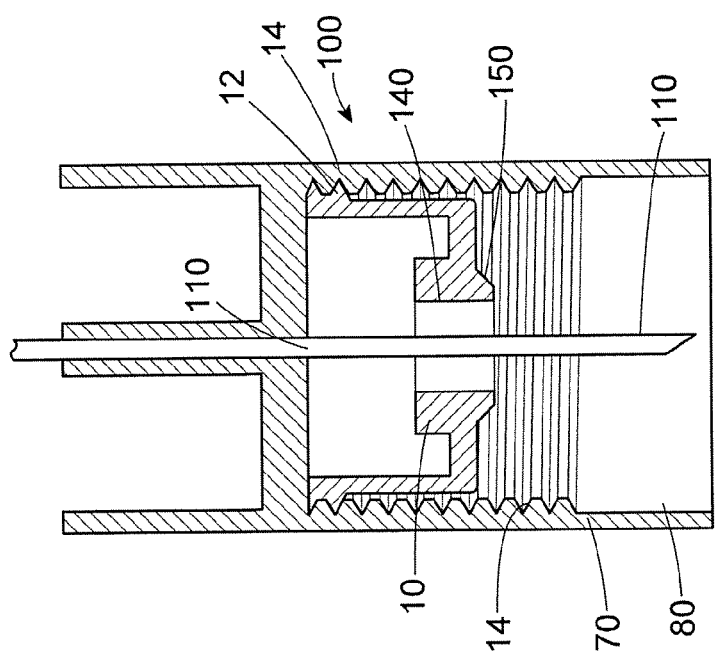
FIG. 1
FIG. 2

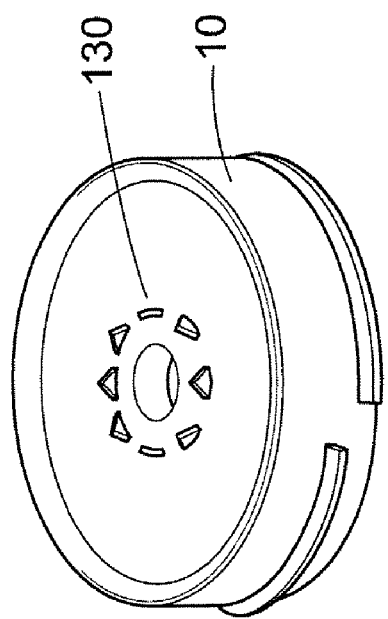
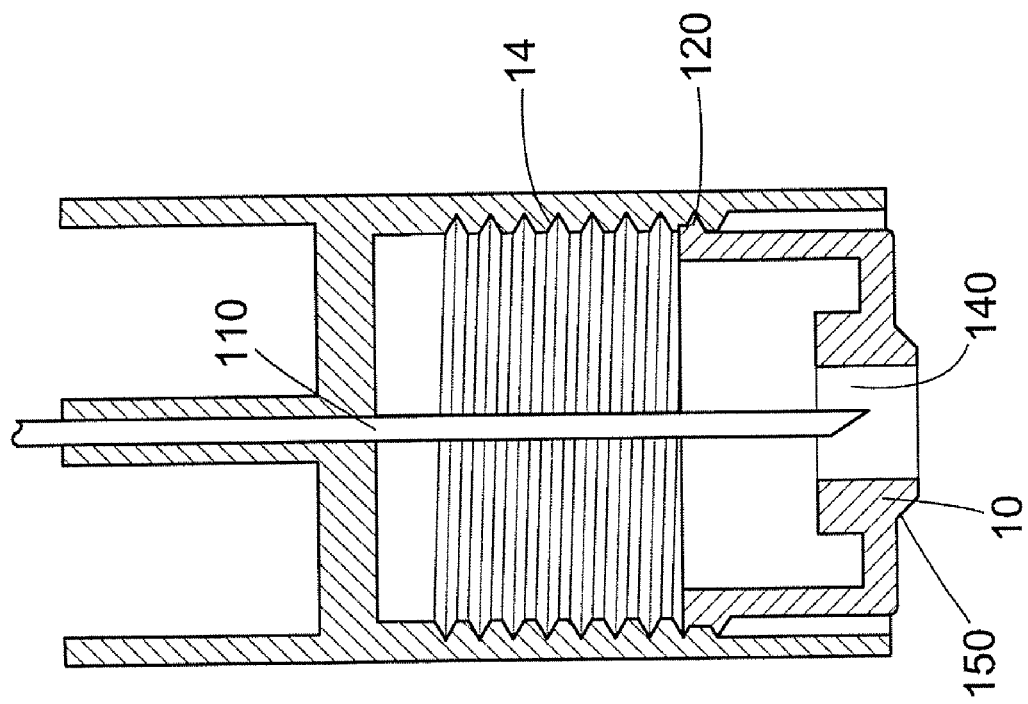

SAFETY PEN NEEDLE WITH NON-INJECTION END PASSIVE SAFETY FEATURES

BACKGROUND OF THE INVENTION

1. Field of the Invention

The invention is directed to a passive safety shield which may be associated with an injection pen needle to shield the non-injection end of the needle.

2. Description of the Related Art

Accidental needlestick injuries from contaminated needles expose healthcare workers to the risk of infection from blood-borne pathogens, including the viruses that cause hepatitis B and C, and HIV. According to the Centers for Disease Control and Prevention, healthcare workers in the United States experience an estimated 600,000 exposures to blood each year, with RNs being subject to an overwhelming majority of these incidents.

While the injection device of choice in the U.S. remains the syringe, the demand for pen needles is growing rapidly. The use of self-injection pen needle devices is increasing due to the relative convenience, portability, and ease of use of these devices as compared to single use syringes. Pen needles are also becoming more commonplace in the hospital/clinical setting, as certain drugs, such as human growth hormone and osteoporosis medications, are available only in pen needle format.

Healthcare workers have sustained needlestick injuries while removing and disposing of needle hubs from pen needle devices after administering an injection to patients. The needles are typically removed after each injection to minimize contamination of the medication in the cartridge and to prevent needle re-use. Removal of the needle generally requires the re-shielding of the needle using the outer protective shield in which it was supplied and it is especially during the re-shielding step where injuries can occur. Needlestick injuries also occur during the removal of pen needles that have not been re-shielded.

U.S. Pat. No. 6,986,760 B2, assigned to the assignee of the present application, the disclosure of which is herein incorporated by reference in its entirety, teaches a pen needle and safety shield system wherein a safety shield, which normally encloses the needle cannula prior to use, permits retraction of the safety shield during injection and automatically extends and locks the shield in the extended enclosed position following use. The pen needle also prevents retraction of the shield during assembly of the shield and needle cannula and hub assembly on the pen injector.

However, this prior art does not disclose a pen needle having a non-injection end passive safety shield. Thus the invention disclosed herein, which may be incorporated into prior art safety shielded pen needles, represents an advance in the art, in that novel means are provided to guard against accidental needlestick from the non-injection end of a needle in a pen needle.

SUMMARY OF THE INVENTION

A non-injection end passive safety shield for an injection pen needle according to the present invention includes a needle hub having a needle mounted thereon, the needle having an injection end and a non-injection end, and the hub having a recess surrounding the non-injection end of the needle to receive a pen injector. A shield member situated on the non-injection end of the hub has an aperture to permit passage of the needle where it passes into the pen injector (and into a vial of insulin carried in the pen injector, for example). The shield member includes an element for engaging the shield member to the pen injector when the pen injector is received by the hub member, so that the shield member moves with the pen injector when the pen injector is removed from the hub to shield the non-injection end of the needle.

Alternatively (or in combination with the engaging element), a biasing element (such as a spring) biases the shield toward the pen injector to insure that the shield covers the non-injection end of the needle when the pen injector is removed from the hub.

BRIEF DESCRIPTION OF THE FIGURES

FIG. 1 depicts a cross-sectional detail of the passive safety shield according to an embodiment of the invention, with the shield member situated within the hub prior to use of the pen needle.

FIG. 2 depicts a cross-sectional detail of the device after the pen injector has been inserted into the hub member, so that the non-injection end of the needle cannula is inserted into a vial carried in the pen injector.

FIG. 3 depicts a cross-sectional detail of the device after an injection has been administered, and the pen injector has been withdrawn and the shield member deployed, so that the shield member shrouds the non-injection end of the needle.

FIG. 4 is a perspective view of the shield member showing elements for engaging the pen injector.

DETAILED DESCRIPTION OF THE PREFERRED EMBODIMENTS

Figure 6:
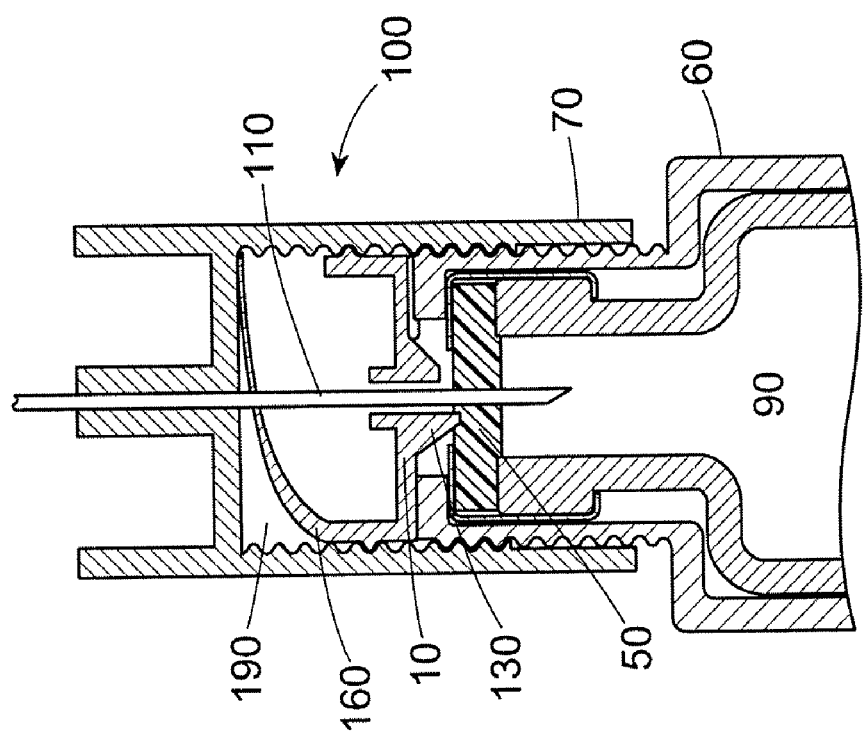
FIG. 6 shows another cross-sectional view of still another embodiment of the device, with a biasing element biasing the shield member in the direction of the pen injector.

The safety shield system according to the invention is "passive" because shielding of the non-injection end is automatic upon removing the pen-injector. User-implemented steps are not required to shield the non-injection end of the needle. The terms "injection end" and "non-injection end" refer to directions on the device. The injection end refers to a direction toward the end of the device that is normally pressed against a patient's body during an injection (the distal end), while the non-injection end refers to the opposite direction, toward the proximal end, whether the patient injects himself or herself, whether someone else administers the injection, and whether or not an injection is actually accomplished.

As used herein, the non-injection end shield "covers" or "shrouds" the needle when the tip of the needle does not extend beyond the end wall of the shield, notwithstanding that the tip of the needle may be quite close to the aperture in the shield, and exposed to view.

As shown in FIG. 2, an injection pen needle 100 generally includes a tubular body referred to herein as pen injector 60 including a vial 90 for holding a fluid, such as insulin, anti-histamines, etc., which may be accessed by the needle 110. In general, except where the context requires otherwise, reference to the pen injector refers to both the outer casework of the injector and the vial within it, or medication may be provided in the pen injector directly, without a vial, without departing from the scope of the invention. A needle hub 70, on which the needle is mounted, receives the pen injector in a cup-shaped recess 80 on the non-injection side of the hub. The hub 70 and pen injector 60 may be threaded to engage one another, or another suitable mating connection may be used. The needle cannula 110 extends into an end portion of the hub 70 and includes a non-injection end extending into the body portion of the pen injector, to pierce the closure of the vial 90. The opposed injection end of the needle is for injection, typically into the patient.

FIG. 1 shows a first embodiment, in which the shield member 10 is situated on the base of the pen needle hub 70 prior to fitting the pen injector. In this case, the needle 110 is not shrouded by the shield 10 when the pen injector is inserted. The shield may have threads 12 engaging with threads 14 on the hub and a small interference element (not shown) or frictional force may be used to prevent the shield moving during distribution and/or prior to use. It will be understood that any force required to retain the shield in this position should be less than the force required to retract the shield into the hub when the pen injector is removed so that the shield moves with the pen injector, as intended.

Alternatively, in an embodiment not shown in the figures, the shield 10 may sit so that it covers or protrudes from recess 80 in the hub 70 covering the non-injection end of the needle before the pen injector is inserted. The pen injector 60 may be engaged with the shield 10, such as with one or more mating tabs and recesses, and then both the shield 10 and the pen injector 60 may be installed into the recess 80, such as by pushing and/or screwing. Prior to engaging the pen injector in the hub, a retaining element may be used to retain the shield in a position covering the non-injection end of the needle. For example, as shown in FIG. 3, a raised portion 120 adjacent the thread may be used to prevent movement of the shield on the thread until the user installs the pen injector. Alternatively, the shield may be held in position by a frictional fit, which is overcome when the pen injector is installed.

Aperture 140 on the shield member 10 permits passage of the needle 110. A raised feature, such as ridge 150 around the aperture 140, may optionally be used to provide additional height to shroud the non-injection end of the needle prior to the user installing the pen injector or after the pen injector has been removed. The raised ridge 150 may be accommodated in a free space immediately above the vial septum area found in prior art pen injector devices. As the rest of the shield 10 may have reduced height compared with the ridge 150, it is easier to accommodate the shield member into the hub of such prior art devices with less modification. Specifically, less height is required in the hub to accommodate the shield.

FIG. 2 shows the shield member 10 in the pen needle hub, with the pen injector tip fully engaged with the hub. The non-injection end of the needle 110 pierces septum 50. In this position, the shield member 10 engages the pen injector 60, so that when the pen is removed, the shield rotates with it and it is drawn into the free space in the hub.

FIG. 3 shows the shield member 10 in its protecting position, where the non-injection end surface provides an effective barrier to accessing the non-injection end of the needle tip. A lockout member (not shown) adjacent the thread on the shield may be utilized to prevent the shield member 10 from retreating into the hub, once the pen injector has been removed. Alternatively, a protuberance on the thread could create an interference such that shield 10 does not move down the threads in the hub. Another lockout element could be provided, as known in the art, to prevent the shield from retreating into the hub.

FIG. 4 shows a perspective view of the shield member 10 having a ring of teeth 130 which engage with the septum of the vial in the pen injector. The teeth 130 drive the shield in the threads in the hub and act as an engaging element to engage the shield 10 with the pen injector 60, or with the septum of the vial inside the pen injector. As an alternative engaging element, one or more adhesive or grippy polymer elements arranged around the surface of the shield member may also be used. When the pen injector is fully screwed (or otherwise securely inserted) into the hub, the engaging element temporarily attaches the shield to the pen injector so that when the pen injector is unscrewed (or otherwise removed) from the hub after an injection has been administered, the shield is rotated (or otherwise moved in tandem) with the pen injector and retracted with it to cover the non-injection end of the needle.

Figure 5:
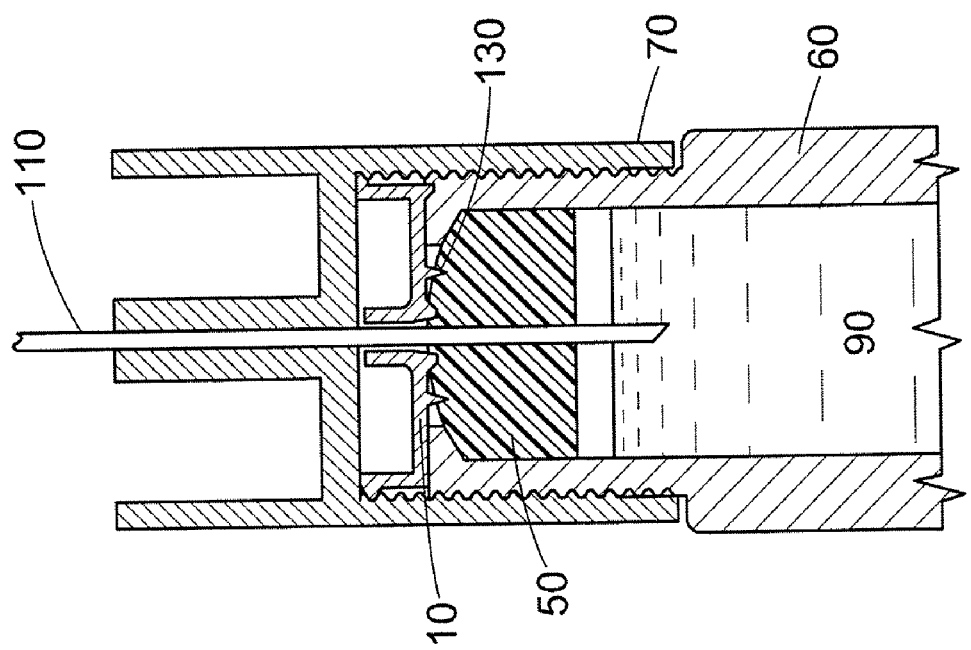
FIG. 5 depicts a cross-sectional view of another embodiment of the device, with the pen injector installed on the hub.

FIG. 5 shows the pen injector 60 fully screwed home. In this state, the teeth 130 on the shield member are engaged with the pen injector's septum, such that as the pen is unscrewed, the rotating of the pen injector causes the shield to rotate with it and so that it can be driven up the thread in the pen needle's hub.

FIG. 6 also depicts the pen injector fully screwed home, and further depicts a biasing member 160 biasing the shield member toward the pen injector in the hub, so that the shield member securely engages the pen injector when the pen injector is withdrawn after an injection has been administered. In FIG. 6, biasing member 160 is shown as being integral with the shield member 10, biasing the shield toward the pen injector and pressing against the inside surface of the injection end of the hub. That is, the shield and biasing member constitute one piece. Such an integral member may conveniently be made from plastic or metal. Alternatively, a separate spring element may be used to bias the shield in toward the non-injection end of the device.

In an alternative embodiment, the spring alone may be used to bias the shield to cover the non-injection end of the needle when the pen injector is removed.

By shielding the non-injection end of a pen needle device, the safety shield according to the invention provides a clear benefit to healthcare professionals in the hospital or clinic setting. The shield may have additional advantages of hiding the needle from view, which is an advantage for patients who are particularly needle-averse. In the non-clinical setting, safe disposal of the needle hub is facilitated according to the invention, as the needle is essentially enclosed once an injection is administered. A particular advantage of the safety shield is its simplicity of use, requiring little or no implementation from the user. Because the shield is built into the hub, there is no cap or other separate cover that can be separated from the device and lost.

A pen needle according to the invention may utilize a range of needle lengths and gauges. In preferred embodiments, the pen needle is small, to minimize patient discomfort, effect a successful injection, and enhance portability and ease of use. Thus, it is contemplated that the shield could effectively be used with 29, 30 and 31 gauge needles having injection lengths of 5 mm, 8 mm and 12 mm, although these examples are not limiting. Visible coding schemes may be added to indicate the type of injection to be administered, the size and gauge of needle, to indicate engagement of the pen injector, that the shield has moved or locked out, etc. The pen needle will, in most cases, be packaged in an outer shield with a foil sterility barrier, as commonly practiced in the art. Alternatively, other packaging to ensure sterility may be provided. These and other improvements and modifications may be made without departing from the scope of the invention, which is defined in the appended claims.

What is claimed is:

1. A non-injection end passive safety shield for an injection pen needle, comprising:
   a needle hub;
   a needle mounted on the hub and having an injection end and a non-injection end, wherein the hub has a recess surrounding the non-injection end of the needle to receive a pen injector;
   a shield member situated on the hub member having an aperture to permit passage of the needle,
      an element including teeth for engaging a surface of the pen injector, or for engaging a surface of a vial within the pen injector to engage the shield member to the pen injector prior to or when the pen injector is received by the hub member, whereby the shield member moves with the pen injector and shields the non-injection end of the needle when the pen injector is removed from the hub.

2. The passive safety shield of claim 1, further comprising threads on the shield member mating with threads on the hub member.

3. The passive safety shield of claim 1, further comprising a raised feature around the aperture in the shield member.

4. The passive safety shield of claim 1, further comprising threads on the hub member to receive threads on the pen injector.

5. The passive safety shield of claim 1, further comprising a lockout element to prevent the shield member from retreating into the hub after the pen injector has been removed.

6. The passive safety shield of claim 2, further comprising a lockout element adjacent the thread on the shield member or the thread on the hub member to prevent the shield member from retreating into the hub after the pen injector has been removed.

7. The passive safety shield of claim 2, further comprising a lockout element to prevent the shield member from retreating into the hub after the pen injector has been removed.

8. The passive safety shield of claim 2, further comprising a retaining element adjacent the thread on the hub, retaining the shield in a position covering the non-injection end of the needle prior to screwing the shield into the hub.

9. The passive safety shield of claim 1, comprising an elastic biasing member to bias the shield member in a direction toward the non-injection end.

10. The passive safety shield of claim 9, wherein the biasing member is integral with the shield member.

11. The passive safety shield of claim 9, comprising the elastic biasing member biasing the shield toward the non-injection end of the needle in addition to an engaging element on the shield engaging a surface of the pen injector, or engaging a surface of a vial within the pen injector, to a surface of the shield.

12. The passive safety shield of claim 1, further comprising a retaining element, retaining the shield in a position covering the non-injection end of the needle prior to engagement of the pen injector.

13. A non-injection end passive safety shield for an injection pen needle, comprising:
   a needle hub;
   a needle mounted on the hub and having an injection end and a non-injection end, wherein the hub has a recess surrounding the non-injection end of the needle to receive a pen injector;
   a shield member situated on the hub member having an aperture to permit passage of the needle,
   an element comprising adhesive material for engaging the shield member to the pen injector or a vial within the pen injector to engage the shield member to the pen injector prior to or when the pen injector is received by the hub member, whereby the shield member moves with the pen injector and shields the non-injection end of the needle when the pen injector is removed from the hub.

* * * * *